(12) United States Patent
Griffin et al.

(10) Patent No.: US 11,911,101 B2
(45) Date of Patent: Feb. 27, 2024

(54) PROCESS AND SYSTEM FOR REDUCING LASER DAMAGE TO SURGICAL INSTRUMENTS

(71) Applicant: Cyclone Biosciences, LLC, Phoenix, AZ (US)

(72) Inventors: Stephen E. Griffin, Peoria, AZ (US); Jason Guth, Tempe, AZ (US)

(73) Assignee: CYCLONE BIOSCIENCES, LLC, Tucson, AZ (US)

( * ) Notice: Subject to any disclaimer, the term of this patent is extended or adjusted under 35 U.S.C. 154(b) by 141 days.

(21) Appl. No.: 17/691,541

(22) Filed: Mar. 10, 2022

(65) Prior Publication Data

US 2022/0192747 A1 Jun. 23, 2022

Related U.S. Application Data

(63) Continuation-in-part of application No. 15/414,706, filed on Jan. 25, 2017, now Pat. No. 11,272,983.

(60) Provisional application No. 62/290,559, filed on Feb. 3, 2016.

(51) Int. Cl.
*A61B 18/26* (2006.01)
*A61B 18/00* (2006.01)

(52) U.S. Cl.
CPC ..... *A61B 18/26* (2013.01); *A61B 2018/00511* (2013.01); *A61B 2018/00982* (2013.01)

(58) Field of Classification Search
CPC .................. A61B 18/20; A61B 18/203; A61B 2018/2035; A61B 2018/20351; A61B 2018/204; A61B 2018/2045; A61B 2018/205; A61B 2018/2055; A61B 2018/20553; A61B 18/22; A61B 2018/2205; A61B 2018/2244; A61B 2018/2247; A61B 2018/2272; A61B 2018/2277; A61B 2018/2283; A61B 2018/2288; G02B 6/42; G02B 6/4286; G02B 6/4296
USPC ..... 606/2.5, 10–18; 359/196.1, 197.1, 199.2, 359/201.2, 202.1, 223.1, 226.1, 226.2, 88, 359/5, 888, 889, 891
See application file for complete search history.

(56) References Cited

U.S. PATENT DOCUMENTS

| | | | | |
|---|---|---|---|---|
| 4,762,385 | A | * | 8/1988 | Fuse .................... G02B 6/4296 385/38 |
| 5,387,211 | A | | 2/1995 | Saadatmahesh |
| 5,621,831 | A | * | 4/1997 | Staver ................. G02B 6/4296 385/33 |

(Continued)

*Primary Examiner* — Ahmed M Farah
(74) *Attorney, Agent, or Firm* — Quarles & Brady LLP; Yakov S. Sidorin

(57) ABSTRACT

Optical fibers used to deliver laser energy inside the body are often twisted and bent when passed through tortuous routes in accessing the target tissue or pathology, e.g. during the ureteroscopic laser lithotripsy. When an irregular laser output that is produced at the start of the lasing process is channeled through a fiber that is bent at or near the bend limit, fail safe polymer claddings are damaged and can no longer contain even regular laser output in tight deflection. A common resulting fiber failure, known as 'fiber burn through', results in injuries to patients and is a major cause of damage to ureteroscopes. Discussed are the systems and methodologies providing a solution to such premature fiber failure.

11 Claims, 4 Drawing Sheets

(56) References Cited

U.S. PATENT DOCUMENTS

| | | | | |
|---|---|---|---|---|
| 5,729,335 A | * | 3/1998 | Green | G01L 5/105 |
| | | | | 356/73.1 |
| 7,400,808 B2 | * | 7/2008 | Seo | G02B 6/02395 |
| | | | | 385/128 |
| 2003/0216717 A1 | * | 11/2003 | Nahen | A61B 18/22 |
| | | | | 606/3 |
| 2015/0268414 A1 | * | 9/2015 | Hayashi | H04B 10/25891 |
| | | | | 385/127 |

* cited by examiner

PROCESS AND SYSTEM FOR REDUCING LASER DAMAGE TO SURGICAL INSTRUMENTS

CROSS-REFERENCE TO RELATED APPLICATIONS

This patent application is a continuation-in-part from the U.S. patent application Ser. No. 15/414,706 filed on Jan. 25, 2017 and published as US 2017/0215961, which in turn claims the benefit of and priority from the U.S. Provisional Patent Application No. 62/290,559, filed Feb. 3, 2016. The disclosure of each of the above-identified patent applications is incorporated herein by reference.

TECHNICAL FIELD

The present invention relates to methodologies of protection of a bent optical fiber, to which optical power from a powerful laser source is coupled during the operation of a laser system containing such lase source, from burning and/or otherwise degrading during the process of carrying this optical power. The goal is achieved by blocking errant and potentially damaging high-level laser energy, which is generated in the interim as the operation of the laser pump feeding the laser source and/or the optical gain medium stabilize or equilibrate to target operational conditions, from being coupled to the target optical fiber, thereby reducing damage to optical fiber coatings and/or lowering the requirement to/threshold for the minimum value of a bend radius for safe delivery of therapeutic energy.

RELATED ART

Lasers find utility in a variety of applications where significant pulse energies or laser powers are delivered to identified targets by optical fibers. One of limitations to delivery of laser power or energy by an optical fiber is the minimum bend radius of the optical fiber, especially in the case where energy loss within or at the bend is sufficient to initiate catastrophic failure of the optical fiber. Generally, under otherwise equal conditions, the minimum optical bend radius depends on the wavelength of the laser light, the average power or peak pulse energy, the repetition rate of the laser output (in case of the pulsed output), and the size and the construction of the optical fiber itself.

Optical fibers with smaller dimensions are often utilized to deliver pulsed laser energy to kidney stones, and operated within highly deflected, spatially bent flexible uretero-scopes. A common failure mode of optical fibers within flexible ureteroscopes is popularly described as a "burn through", where the fiber suddenly fractures within the scope forceps channel. Such failures are a leading cause of costly scope repairs and have even been known to injure patients by burning through the damaged scope wall.

Another common optical fiber failure is caused by the surgeon's gripping the fiber to control its position within the patient; if the minimum operational optical bend radius is exceeded, the fiber burns through and the released optical power may injure the surgeon.

SUMMARY

Embodiments of the invention provide a process for preventing a damage of a bent optical fiber configured for transmission of light generated by a laser source therethrough. Such process includes a step of switching "on" a laser source to generate a laser output of a chosen duration directed towards and aligned with the bent optical fiber, while keeping a useful amount of light from the laser output that is coupled into such optical fiber below an operational level starting at a moment of the switching and for a period of time, to prevent an errant portion of the laser output from being coupled into such optical fiber. The action of keeping the useful amount of light below the operational level is carried out by one or more of (i) keeping an amount of seed energy transferred to a gain medium of the laser source from a pump system below a pump level required for the laser source to generate the laser output at the operational level, and (ii) attenuating the useful amount with the use of with a beam attenuator positioned in an optical path of said laser output between the laser source and the bent optical fiber (here, the beam attenuator includes at least one of a beam absorber, a beam splitter, and a beam shutter). The process additionally includes a step of increasing the useful amount of light substantially to the operational level by, respectively, transferring the amount of seed energy from the pump system to the gain medium substantially at the pump level and/or reducing a degree of the attenuating. (This step is performed after the period of time during which the useful amount of light was kept below the operational level has lapsed).

Embodiments of the invention additionally provide a process for preventing a damage of a bent optical fiber configured for transmission of light generated by a laser source therethrough. This process includes a step of switching "on" a laser source to generate a laser output of a chosen duration directed towards and aligned with the bent optical fiber, while keeping a useful amount of light from the laser output that is coupled into the optical fiber below an operational level starting at a moment of the switching and for a period of time, to prevent an errant portion of the laser output from being coupled into said optical fiber. The action of keeping the useful amount of light below the operational level can be performed by attenuating the useful amount with the use of with an optical beam splitter positioned in an optical path of the laser output at 10° to 80° with respect to the optical path between the laser source and the bent optical fiber. The process further includes a step of increasing the useful amount of light substantially to the operational level by reducing a degree of the attenuating to couple an un-attenuated laser output into the bent optical fiber. (This step is performed after the period of time—during which the useful amount of light was kept below the operational level—has lapsed).

BRIEF DESCRIPTION OF THE DRAWINGS

For a more complete understanding of the disclosure, reference should be made to the following detailed description and accompanying drawing figures, of which.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another. The Drawings are intended to be illustrative and to not limit the scope of the invention.

DETAILED DESCRIPTION

Figure 1:
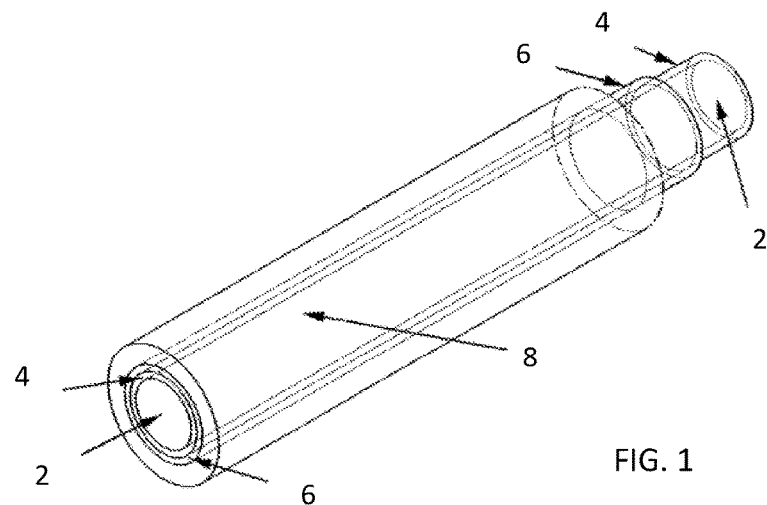
FIG. 1 is an isometric schematic illustrating constructions of a typical holmium laser lithotripsy optical fiber.

Optical fibers are often utilized in delivering energy, for ablating and fragmenting urinary and biliary calculi, vaporizing diseased tissues, cutting and joining materials, generating plasmas for speciation of materials, and other surgical and non-surgical applications. Where the optical fiber is tasked to follow a tortuous path, for example in accessing urinary calculi located with a lower pole renal calyx, the minimum value of a bend radius for the fiber that will still allow the satisfactory operation of the fiber may be exceeded. FIG. 1 schematically illustrates a structure of the fiber that is often used in surgical applications to deliver light to a target tissue. The fiber core 2 is surrounded by a doped glass cladding 4 (similarly to many other optical fibers). A polymer coating 6, forming an over the glass cladding, is selected to have a lower refractive index than that of the glass cladding 4 and to be appropriately transparent at the laser wavelength(s) of interest. A buffer layer 8 of polymer (typically ethylene tetrafluoroethylene copolymer, a polyamide or polyamide/imide copolymer, a polyaryletherketone or a similar polymer) covers the polymer coating 6.

Such "double clad" fibers contain light that is, while transmitted through a bent fiber, propagates at higher and higher angles to the fiber axis (up-converted to higher angles of propagation) in tight bending region(s) (FIG. 2) by virtue of the higher numerical aperture (NA) provided by the polymer cladding 6. Polymers used for the cladding 6 are not as transparent as the glass fiber at many wavelengths of light generated by typical surgical lasers (e.g. an approximately 2000 nm emission from a thulium laser and approximately 2100 nm emission from a holmium laser), so some of light propagating through the fiber at high angles is likely to penetrate into the polymer layer and be absorbed and converted to heat. If too much light leaks from the glass cladding 4, the secondary cladding 6 suffers thermal damage. Damaged—even if moderately—polymer cladding 6 is, understandably, structurally weakened and cannot contain additional leakage of optical power.

Figure 2:
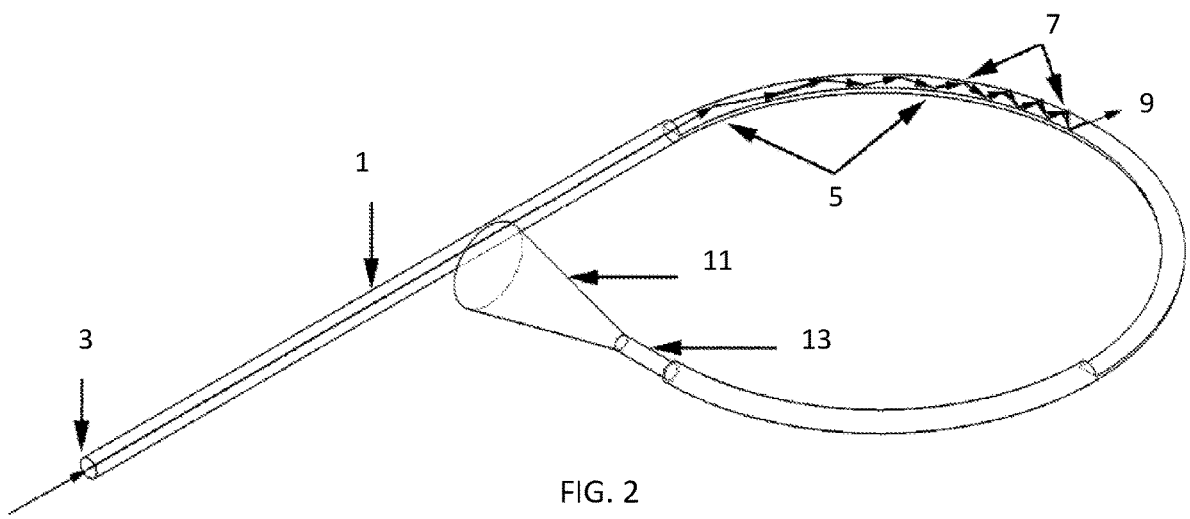
FIG. 2 illustrates, in an isometric view, mode promotion, cladding modes, and leakage of light in a bent optical fiber.

The schematic of FIG. 2 depicts the change of angles at which light propagates through the bent optical fiber (angular up-conversion) beyond the containment provided by the secondary cladding in an illustration commonly followed in related art, where light is launched into the fiber 1 at the input face 3 and exits 11 at the working tip 13. The standard, conventional understanding is that where the fiber 1 is bent too tightly, the angle of propagation of laser light (viewed through the prism of a total-internal-reflection model, according to which light "reflects" at the core-to-glass-cladding interface) increases, 5, until the maximum angle for total internal reflection is exceeded and the light starts 'reflecting' at the glass-to-polymer interface. If the angle 7 of propagation of light continues to increase within the tightly curved fiber, such angle may exceed the maximum angle for total internal reflection at the glass-to-polymer interface and escape from the bounds of the optical fiber, 9.

Figure 3:
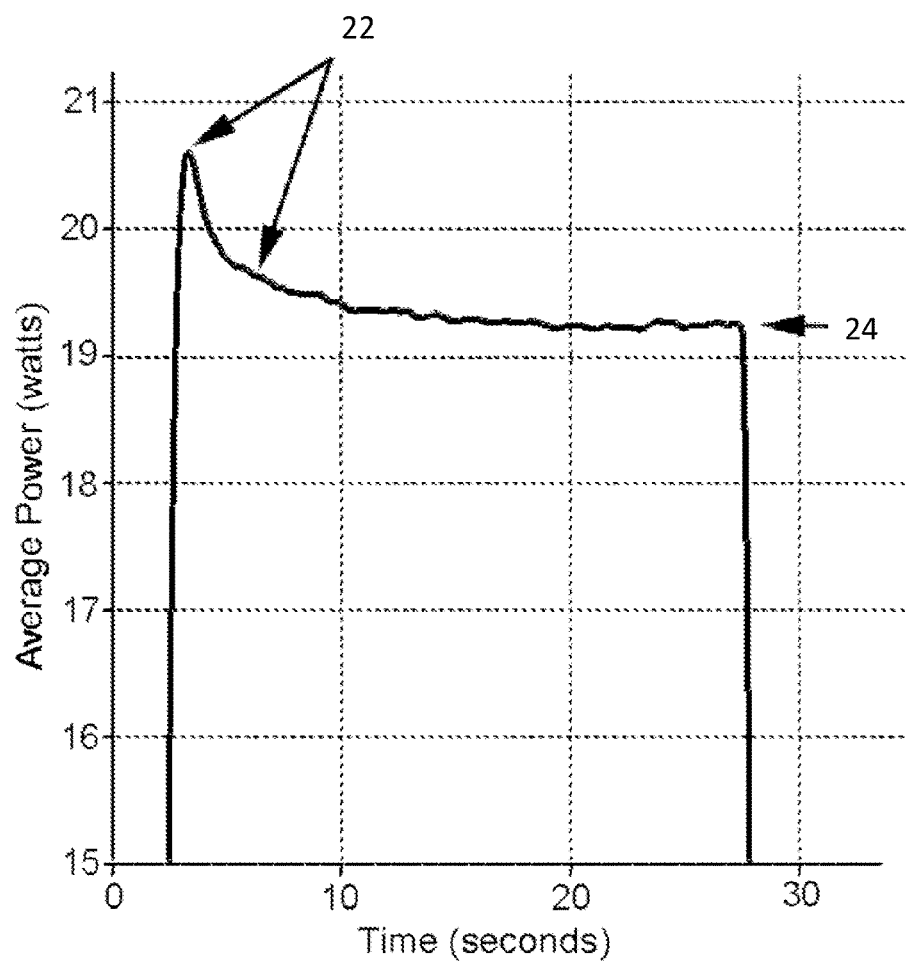
FIG. 3 is a plot depicting evolution of a typical pulse of light produced by a conventional holmium laser.

The idea of the present invention is rooted in a more thorough treatment of the failure mechanism than that provided by the standard model. Many laser sources that produce sufficient laser energy or power to carry out the desired task (whether surgical or non-surgical) are somewhat operationally unstable at the beginning of the light emission process—approximately within the first half second to several seconds from the beginning of emission (FIG. 3), where the laser produces significantly higher pulse energies or average powers 22 that those operationally targeted, and/or laser output beams with lower $M^2$ beam quality than operationally intended (the latter including hot spots and high order spatial modes that may be damaging to optical fiber coatings, particularly when the optical fiber is bent at, or near, the optical minimum bend radius). Once this initial portion of the laser output is coupled into the optical fiber and damages the bent portion of such fiber, the normal, targeted laser output 24 traversing the damaged fiber is less effectively contained by the damaged secondary coating, leading to fiber failure even at larger bend radii and even at lower levels of power or energy than would otherwise cause fiber failure. Notably, the value of a bend radius at which the damage of the optical power becomes possible generally varies with the fiber size and composition, the laser wavelength, and the mode distribution within the fiber, and the damage caused by the early and unstable laser output occurs at a larger bend radius than that at which the fiber fails under normal (or stable) laser output.

This proposed interpretation of the failure model of fibers delivering power through tight bends is the fruit of observations made while testing holmium laser surgical fibers for safe minimum bend radii in validating new fiber optic termination designs. One test that was performed was the active bend test, where the fiber was progressively bent to tighter radii while continuing to deliver/channel laser power. It was noted that when the initial fiber bend radius (prior to activation of the laser) was at or near the optical minimum bend radius, the fiber failed at a larger radius (in some cases, at approximately twice the optical minimum bend radius).

A modification of the active bend test provided additional support for the new failure model. Here, when the laser emission was paused near to, but before the failure point average for like fibers, the fiber failed within the first few pulses after the laser was activated again.

Furthermore, when light delivered by the first several pulses of the laser was manually blocked (for example, with a slab of graphite), no difference was observed in the bend radius at failure between fibers used in the active bend testing at different initial radii.

In surgical use, fibers are subjected to both active and static bending and lasing intervals are often brief and sporadic. The methodologies discussed in this disclosure include strategies for eliminating premature failure of the bent optical fiber and turn on the idea of attenuating the very beginning of the laser emission after the moment when the laser is activated to prevent this errant laser output from propagating through the bend of an optical fiber altogether. In cases where the divergent from the target parameters output is due exclusively, or almost exclusively, to the instability of the pump source seeding the laser of the laser system instability, blocking the lasing medium from exposure to the first, initial portion of emissions of the pump was also proven to be effective. Where the initial instability was characterized by greatly reduced $M^2$ beam quality (for example, in the form of high order spatial modes generated right after the activation of the laser system) rather than simply higher energy output and hot spots, spatial filtering may be sufficient to prevent higher order modes coupling to the fiber core. Understandably, in the most general case any combination of the proposed approaches can be employed.

Figure 4:
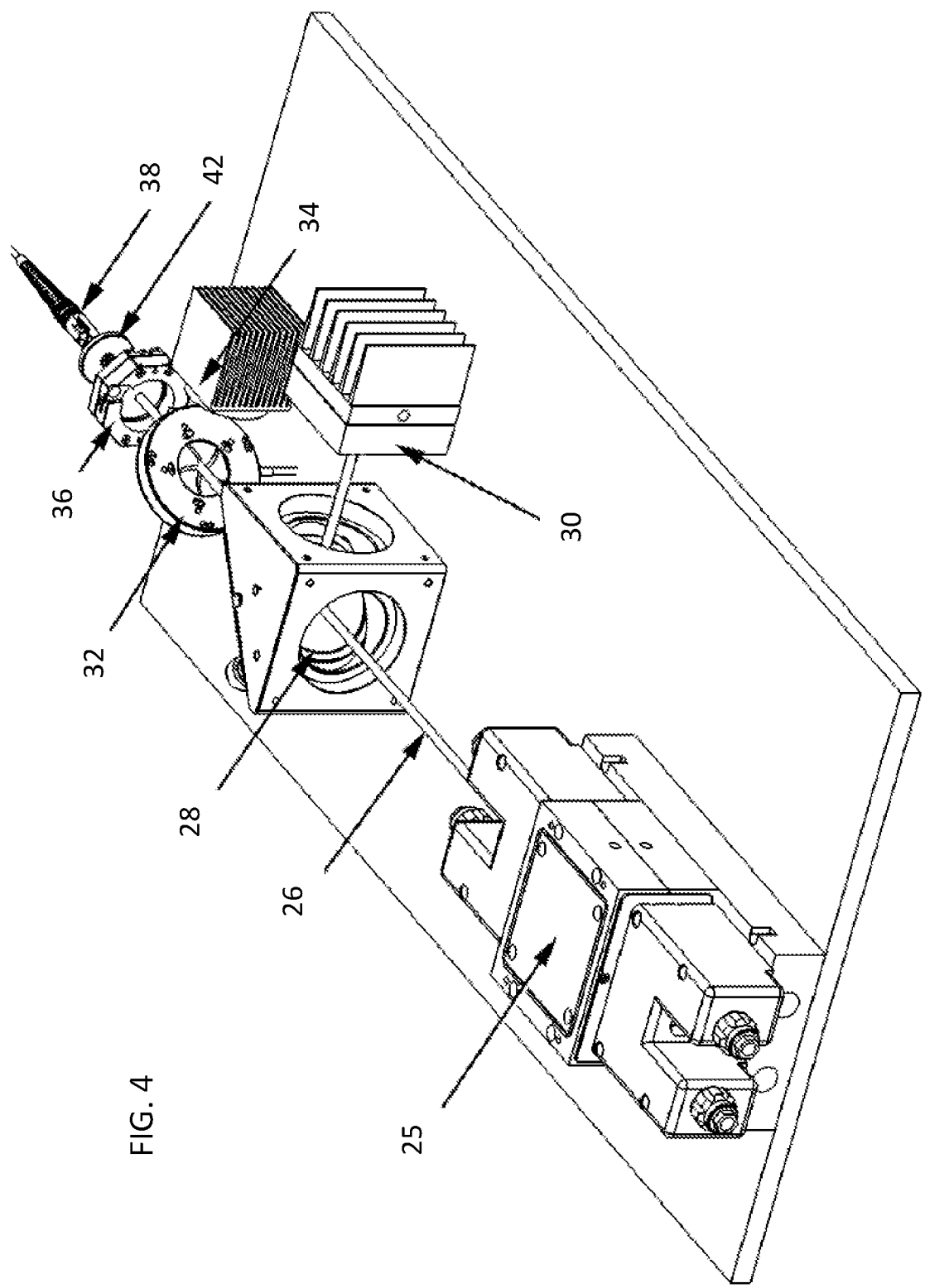
FIG. 4 shows, in an isometric view, an embodiment of a laser system employing a surgical laser source (such as a holmium laser, for example).

FIG. 4 illustrates a layout of a typical laser system employing a holmium surgical laser where the laser head 25 (or 'brick') is configured to produce a beam 26 directed to pass through the beam splitter 28 to have a small portion of the beam 26 reflected into a power meter 30 (alternatively called an energy meter or a monitor). A shutter 32, disposed along the path of the portion of the beam 26 that passes through the beam splitter, reflects the light towards a beam dump 34 when closed (as depicted) but let's the beam pass through the shutter to define the functional beam path of interest. When the shutter 32 is opened, the beam is focused by a mounted focusing optic 36 onto an optical fiber 38 housed within a fiber connector and installed at the laser port 42.

Figure 5:
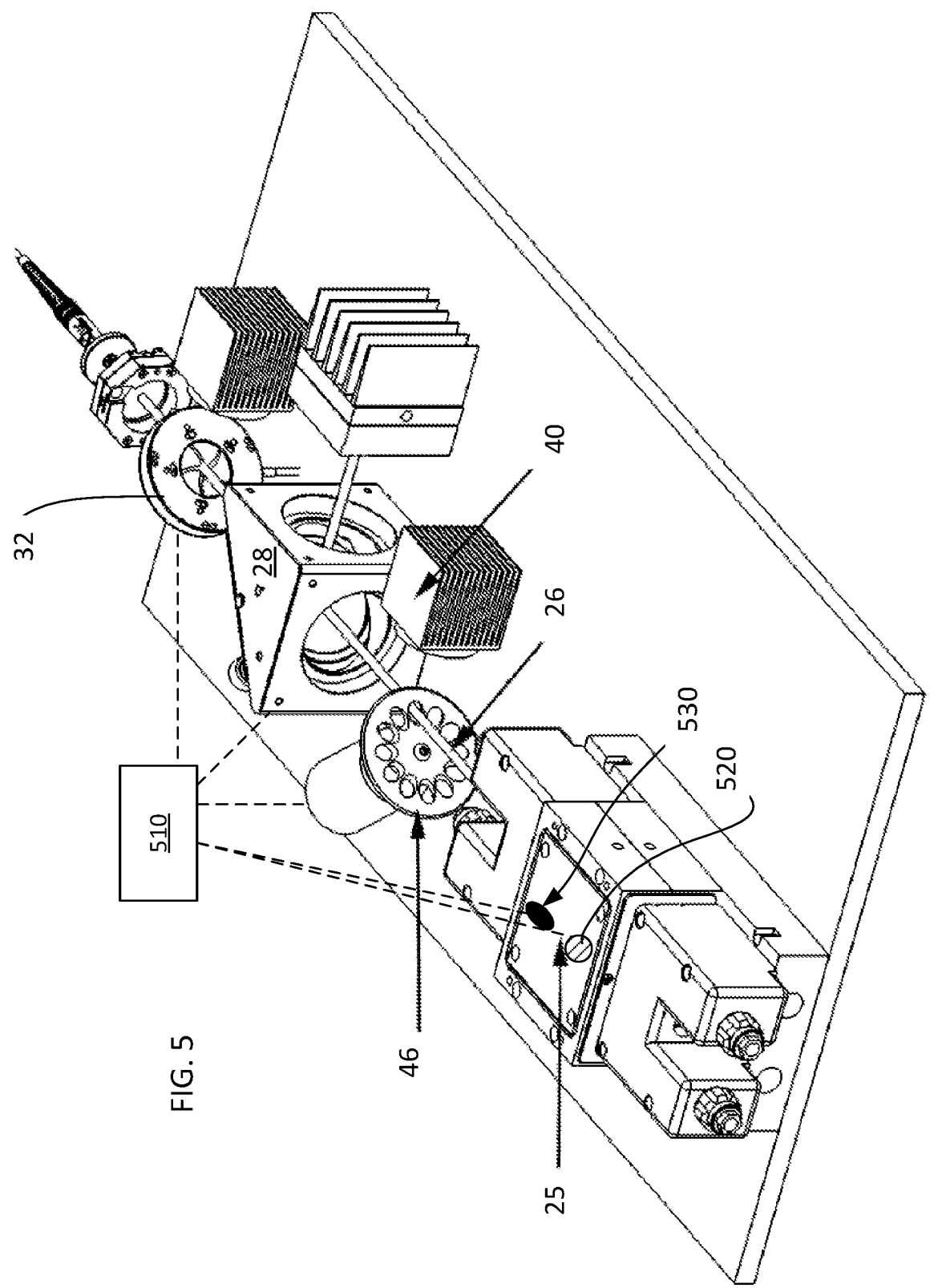
FIG. 5 is an isometric view of the embodiment of FIG. 4 equipped with a chopper blade.

FIG. 5, schematically presenting on non-limiting embodiment 500 of the invention, illustrates the layout that is substantially similar to that of FIG. 4 but with the addition of a spatial beam interrupter or chopper 46. As shown in the example of FIG. 5, the beam interrupter or chopper may be configured to include a substrate (which can be reflective and/or absorptive at a wavelength of the laser output beam 26, which make such beam chopper a beam splitter/reflector and/or a beam absorber) that is configured to include openings or apertures (dimensioned to pass the beam 26 through) that are separated from one another with a body of the substrate such that, when the beam interrupter is oriented to intersect the beam 26 at one of the openings or apertures, the beam 26 is not spatially interrupted and continues to carry light energy towards the focusing optics 36. On the other hand, when the beam interrupter 46 is oriented such as to intersect the beam 26 with a reflective or absorptive portion of the body of the substrate, the beam 26 is substantially blocked from propagating pass the interrupter towards the focusing optics 36. It is appreciated therefore, that the beam interrupter is configured as a beam deflector and/or a beam absorber. In a specific non-limiting example of FIG. 5, the beam interrupter 46 is shown configured as a chopper blade disposed at an angle with respect to the optical path of the beam 26 (for example, at 45 degrees). In this specific embodiment, the beam interrupter/chopper blade is dimensioned to contain a plurality of oversized (relative to the laser beam) holes (which are the openings or apertures of the beam interrupter). In operation, when the chopper blade is rotated at a predetermined speed and if the body of the chopper blade is configured as a beam splitter (that is, the body of the chopper blade is made at least partially reflective), this chopper blade thereby attenuates the beam 26 by reflecting light from the beam 26 into a beam dump 40 (or beam sink) during part of the revolution period while permitting the light to pass through the chopper blade during the remaining part of the revolution period. In at least one implementation, the chopper blade 46 may be programmed to stop in a reproducible rotational position such as to have the not attenuate the beam. Understandably, the chopper blade need not have this specific construction in order to function and, in fact, may be equipped with a spatially filtering aperture for passing the beam in the stopped position, or a larger hole at the stopped position to ensure that no spatial filtering of the beam 26 occurs when the blade is stopped, depending upon laser output stability characteristics.

The implementation of the idea of the invention can be carried out with the shutter or switch 32 of the embodiment 500, Such shutter may be configured to be a mechanical shutter (as shown) or as an opto-electronic shutter (for example, configured to operate as an electrooptical shutter as known in the art), to name just a few, to block the beam from passing through the shutter 32 when required. Appropriately re-configuring the conventionally-structure shutter 32 such as to enable the overall system to delay the opening of the shutter 32 of a conventional arrangement of FIG. 4 with the use of, for example, an appropriate programmable microprocessor 510 (appropriately programmed electronic circuitry, see FIG. 5) and the appropriately configured program code (software) may be one of the solutions according to the idea of the invention. (Coordination of the operation of the shutter 32 with the use of the processor 510 is indicated, in FIG. 5, with a dashed line connecting the two.) However, such solution may not be bullet proof as in some cases—specifically in the case of using surgical lasers—such solution may yield undesirable results due to a potential conflict between the primary, conventional purpose of such shutter (which is to operate as a failsafe against uncontrolled emission, as mandated by regulatory authorities, rather than as a means for active modulation of the laser beam) and the pre-programmed goal of attenuation of the emission from the laser source as per the idea of the invention. Generally, however, appropriate program code to gently reduce the level of attenuation of the laser output reaching the optical power maybe effective in specific laser designs where $M^2$ beam quality is not a major component of the damaging early portion of the emission of the laser source and if the output laser energy rise is gradual enough. In addition, time need not be the variable for determining when it is appropriate to remove diversion or attenuation from the beam path: the laser power may be monitored before a diverting element and before or after an attenuation mechanism to determine when it is safe to allow the full laser output to pass to the fiber aperture.

Alternatively, attenuation or blocking of the laser output 26 may be accomplished at the pump system 520 of the embodiment 500 (schematically indicated as a patterned circle) that feeds the gain medium 530 (schematically shown as a black ellipse) of the laser head 25. For example, when the pump system 520 is structured as an optical system delivering a seed light to the gain medium 530 of the surgical laser 25, appropriate reflectors may be arranged within the head 25 to temporarily block or attenuate emission produced by the pump system 520 from being delivered to and stimulating laser emission within the gain medium 530, and/or the pump system 520 may be actuated at something less than the full operational pump level required for the initiation of target laser emission 26 at the laser system 25. Most practically, control of such operation of the head 25 is carried out with the use of the programmable processor 510 (which is schematically indicated with dashed lines connecting the processor 510 with the appropriate elements of the laser head 25). Additionally or alternatively, related embodiments of practical solutions to attenuate the laser beam 26 when desired include a reflector to completely divert the beam 26 during the period of unstable laser output, and/or a beam splitter to temporarily attenuate the beam 26, and/or a stationary spatial filter that is reflective and/or absorptive, and/or the use of a movable neutral density filter, and/or the use of a movable chopper blade.

Therefore, one embodiment of the invention includes a laser source aligned with an optical fiber that in operation is bent; a beam attenuator (which, in reference to the schematic of FIG. 5 may include at least one of the beam absorber, 46, beams reflector, 28 and/or 46, and beam shutter, 32) configured to keep or maintain—for a predetermined amount of time—a useful amount of light from the output generated by the laser source received by the optical fiber below an operational level (in order to prevent an errant portion of the laser output from being coupled into the optical fiber) by attenuating a beam of light delivered from the laser source to the optical fiber; and a controller (in reference to FIG. 5—for example, controller utilizing the programmable processor 510) configured to adjust a degree of such beam attenuation. Preferably, but not necessarily, the system is a surgical laser system; for example, an endoscopic laser surgical system comprising, at a minimum, a laser, an optical fiber and an endoscope. As the person of ordinary skill in the art will readily appreciate, the operational level of useful light received at the optical fiber from the laser source is defined as that which, upon the coupling of light into the optical fiber, provides energy transferred through the optical fiber to a defined target to be sufficient to perform the operation or action for which the laser system has been designed. In one specific case, the operation level of light received at the optical fiber of the system can be defined by a substantially un-attenuated beam 26 generated by the laser source upon the period of operation of the laser source associated with generation of the errant portion of the laser output has ended.

In one instance, the laser source can be a holmium laser. In another instance, the fiber includes a bend with a bend radius at about an optical minimum bend radius; preferably, the optical minimum bend radius for a system utilizing a holmium laser. In yet another instance, the controller can be configured to reduce beam attenuation after about 0.1 to about 20 seconds.

The beam attenuator is, preferably, positioned along a beam path from the laser source to the optical fiber and generally includes (i) a beam splitter and a beam sink (for example, a beam sink trap with a heat sink) and/or beam monitor disposed to receive a portion of light output deflected by the beam splitter and/or a beam absorber. In one preferable instance, the system may be complemented with a controller or programmable processor (such as programmable electronic circuitry) configured to remove the beam splitter or the beam absorber portion of the beam attenuator from the beam path.

Figure 6:
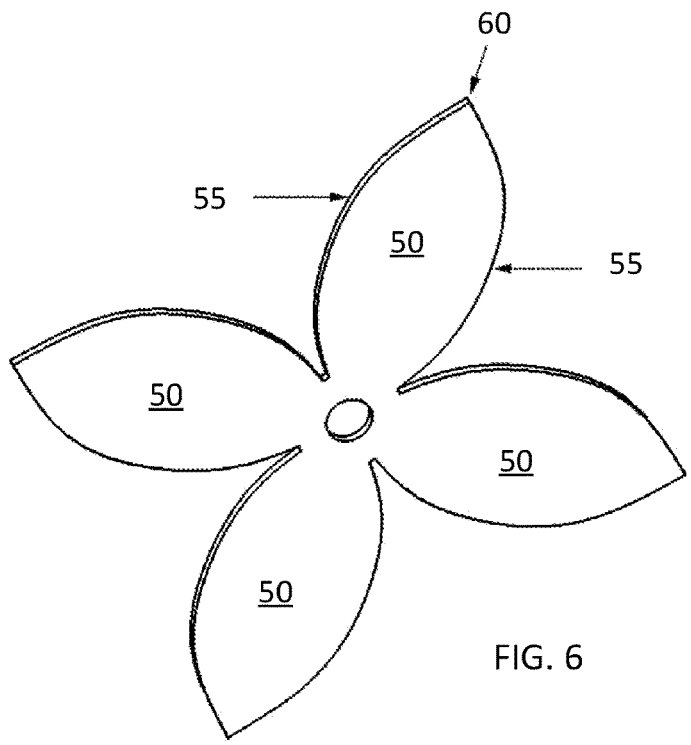
FIG. 6 is an isometric view of a specialized chopper blade.

The beam attenuator may be positioned across the optical path of the beam 26 at a chosen angle. The beam attenuator can be configured as a stationary or moveable reflector (beam splitter) or absorber and, in one specific case, as an optical chopper. In one instance, the beam splitter includes an optical chopper positioned at an angle of between about 10° to about 80°, about 20° to about 70°, or about 30° to about 60° relative to the beam path. That is, the rotational axis of a wheel of the optical chopper is about 10°, 20°, 30°, 40°, 45°, 50°, 60°, 70°, or 80° off of the beam path. In another preferable instance, the beam sink is configured to capture light reflected from the beam-splitting body of the optical chopper. In a one specific case, illustrated in FIG. 6, the optical chopper includes a chopper wheel that possesses vanes 50 having non-radial edges 55. That is, the edges of the vanes of the chopper wheel 9 which vanes may be reflective and/or absorptive) are not radial edges (not linearly extending from a center point) but preferably converge at the outside edge of the chopper wheel 60. In one instance, the vanes 50 have curved edges 55 that converge at the outside edge 60 of the chopper wheel. In still another instance, the beam attenuator that is configured as an optical chopper can be a tuning fork optical chopper. Preferably, the percentage of the beam blocked by the optical chopper can be adjusted by the controller. Not expressly shown in FIG. 4 is the controller and/or a bearing arrangement configured to reversibly reposition the element 46 across the optical path of the beam 26 between first and second positions (here, in the first position the body of the element 46 is disposed to intersect the optical path, and in the second position the body of the element 46 is removed from the optical path substantially completely).

When the embodiment is equipped with the beam monitor, such monitor that is configured to measure output from the laser source. The monitor can measure the beam power, the beam profile, coherency, or combinations of these beam characteristics based on received at the monitor a portion of the output beam 26. Preferably, the monitor provides an output identifying the beam characteristics. In one instance, the controller is configured to reduce beam attenuation pursuant to this output from the monitor. In another instance, the controller is configured to remove the beam attenuator from the beam path when the output from the laser source is within 10%, 5%, or 1% of an output standard.

Furthermore, and referring now to the element 28, such element—if present in an embodiment of the present system—can be also additionally equipped with means to reversibly translating the element 28 into and out of the beam 26.

In a related embodiment, the system can include a laser source optically coupled to the target optical fiber, the laser source including a laser rod and a pump source providing seed light for the operation of the laser source; a beam attenuator unit configured to keep or maintain—for a predetermined amount of time—a useful amount of light from the output generated by the laser source received by the optical fiber below an operational level (to prevent an errant portion of the laser output from being coupled into the optical fiber) by limiting a transfer of energy from the pump source to the laser rod thereby causing the controllable attenuation of the output beam 26 from the laser source 25 and, therefore, of the amount of laser light delivered to the optical fiber (and covered to the optical fiber when the laser source is appropriately optically aligned with the optical fiber). Additionally, the system may include a controller configured to adjust an amount of energy transferred from the pump source to the laser rod (for example, to reversibly reduce this amount below the level required by the laser system for proper operation).

In one instance, the pump source can be at least one diode (e.g., laser diode or pump diode). Here, attenuating the laser pump can include reducing the number of diodes pumping the laser rod and/or reducing (e.g., blocking) a percentage of light from the pump source from reaching the laser rod.

In another instance, the pump source can be one or more flash lamps. Notably, variation of the operation of the laser pump can include reducing the number of flash lamps pumping the laser rod and/or reducing the amount of light reaching the laser rod from the flash lamps.

Preferably, the embodiment of the system is configured as a surgical laser system; for example, an endoscopic laser surgical system. In one instance, the laser system may additionally include a monitor configured to characterize characteristic(s) of the output from the laser source.

It is understood that embodiments configured to temporarily keep or maintain a useful amount of light from the output generated by the laser source received by the optical fiber below an operational level (in order to prevent an errant portion of the laser output from being coupled into the optical fiber) are not mutually exclusive and can be implemented at the same time or independently from one another. In other words, the temporary limitation or reduction of seed/pump energy transferred from the pump source to the laser rod of the laser source and the operation of the attenuator of the beam 26 forming the output from the laser source can be combined.

The temporary reduction of amount of light from the laser source reaching the optical fiber can be effectuated for a period of time T1 beginning when the laser output beam is initiated; then ending the attenuation of the beam while continuing to provide the beam along the beam path. In one preferred instance, the optical fiber is a surgical fiber, for example a flexible endoscope-compatible optical fiber. While the period of time during which the beam is attenuated (T1-period) can vary, the T1-period is preferably shorter than 50%, 40%, 30%, 20%, or 10% of the pulse duration when the laser source operated in the pulsed regime. In one instance, the T1-period is about 0.01 to about 20 seconds; about 0.25 to about 10 seconds; or about 0.5 to about 5 seconds. In yet another instance, the beam quality (e.g., such parameters as power; spatial profile measured, for example, by the $M^2$ parameter; and/or coherence) can be monitored and the T1-period is determined based on the deviation of the beam quality from an output standard. For example, the beam quality can be monitored at a location along the beam path prior to the optical fiber. For example, the T1-period may be terminated when the monitored beam quality parameter is observed to deviate from the predetermined threshold level of such beam quality parameter by no more than 25%, 20%, 15%, 10%, or 5% depending on the specifics of the particular implementation.

In one specific case, the beam attenuator may include a stationary spatial reflector that can be a V-groove reflector and/or a comb reflector. Notably, the term stationary spatial reflector does not convey that the position of the reflector cannot be changed (i.e. the process still can allow for removal of the reflector from the beam path to end attenuation) but that such reflector is not in motion while affecting the attenuation of the beam.

In yet another example, attenuating the beam can include attenuating the laser pump. For example, attenuating the laser pump can be affected by reducing an amount of light reaching the laser rod from the pump source.

A person of ordinary skill in the art will readily appreciate that references throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. Accordingly—as the skilled artisan will readily appreciate—while in this specification the embodiments have been described in a way that enables a clear and concise specification to be written, it is intended that substantially none of the described embodiments can be employed only by itself to the exclusion of other embodiments (to the effect of practically restriction of some embodiments at the expense of other embodiments), and that substantially any of the described embodiments may be variously combined or separated to form different embodiments without parting from the scope of the invention.

Features of the specific implementation(s) of the idea of the invention have been described with reference to corresponding drawings, in which like numbers represent the same or similar elements wherever possible. In the drawings, the depicted structural elements are generally not to scale. No single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed.

For the purposes of this disclosure and the appended claims, the expression of the type "element A and/or element B" has the meaning that covers embodiments having element A alone, element B alone, or elements A and B taken together and, as such, is intended to be equivalent to "at least one of element A and element B".

Embodiments of the invention have been described as preferably including a (micro)processor—in one case, a computer processor—controlled by instructions stored in memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

Disclosed aspects of the invention, or portions of these aspects, may be combined in ways not necessarily listed above and may be appropriately varied without substantial change of the scope of the invention. Accordingly, the invention should not be viewed as being limited to the disclosed embodiment(s).

The invention claimed is:

1. A process for preventing a damage of a bent optical fiber configured for transmission of light generated by a laser source therethrough, the process comprising:
   (i) switching on a laser source to generate a laser output of a chosen duration directed towards and aligned with said optical fiber while keeping a portion of said laser output that is coupled into said optical fiber below an operational level, to prevent an errant portion of the laser output from being coupled into said optical fiber, wherein said keeping is maintained for a period of time starting at a moment of the switching, and
   wherein said keeping the useful amount of light below the operational level is carried out by at least one of:
      (1a) keeping an amount of seed energy transferred to a gain medium of the laser source from a pump system below a pump level required for the laser source to generate the laser output at the operational level, and
      (1b) attenuating said useful amount of light with the use of a beam attenuator positioned in an optical path of said laser output between the laser source and said optical fiber, the beam attenuator including at least one of a beam absorber, a beam splitter, and a beam shutter;
   and
   (ii) after said period of time, increasing the useful amount of light substantially to the operational level by, respectively, transferring the amount of seed energy from the pump system to the gain medium substantially at the pump level and/or reducing a degree of said attenuating.

2. The process according to claim 1, wherein said switching on the laser source includes switching on the laser source to generate a pulsed laser output that is aligned with said optical fiber.

3. The process according to claim 1, wherein the period of time is within a range from 0.01 second to 20 seconds.

4. The process according to claim 1, wherein said switching includes switching a holmium laser or a thulium laser to generate a pulsed laser output at a wavelength suitable for surgical applications.

5. The process according to claim 1, further comprising monitoring a power of said laser output at a location along the beam path and prior to said optical fiber.

6. The process according to claim 5, wherein said laser output is a pulsed laser output, and wherein said reducing includes reducing the degree of attenuation when an average power of said pulsed laser output reaches a value within 10% of an average power of said pulsed laser output.

7. The process according to claim 1, wherein the keeping includes preventing less than 50% of the laser output from being coupled into said optical fiber with the use of a beam attenuator placed in an optical path of the laser output.

8. The process according to claim 1, wherein said attenuating the useful amount of light with the use of with a beam attenuator includes attenuating light with the beam attenuator that is movably disposed across the optical path of the laser output.

9. The process according claim 8, wherein the at least one of the beam absorber and the beam reflector includes an optical chopper positioned across optical path of the laser output at 10° to 80° relative to the optical path.

10. The process according claim 1, comprising coupling the laser output into said optical fiber that is configured for use in an ureteroscopic laser lithotripsy.

11. The process according to claim 10, wherein the attenuating includes chopping said laser output with the optical chopper a body of which includes a substrate that is reflective and/or absorptive at a wavelength of the laser output, the substrate containing an array of throughout openings, each opening dimensioned to substantially pass a beam of light representing said laser output.

* * * * *